United States Patent [19]

Randles et al.

[11] Patent Number: 5,471,000
[45] Date of Patent: Nov. 28, 1995

[54] PROCESS FOR THE MANUFACTURE OF AMINOMETHANEPHOSPHONIC ACID

[75] Inventors: Kenneth R. Randles; Paul G. LeGras, both of Huddersfield, England

[73] Assignee: Zeneca Limited, London, United Kingdom

[21] Appl. No.: 217,399

[22] Filed: Mar. 24, 1994

[30] Foreign Application Priority Data

Apr. 7, 1993 [GB] United Kingdom ............ 9307235

[51] Int. Cl.$^6$ ................................................. C07F 9/38
[52] U.S. Cl. .................................................. 562/16; 562/17
[58] Field of Search ................................... 562/16, 17

[56] References Cited

U.S. PATENT DOCUMENTS

| 2,304,156 | 12/1942 | Engelmann et al. | 260/403 |
| 4,044,006 | 8/1977 | Weil | 544/67 |
| 4,094,928 | 6/1978 | Gaertner | 260/944 |
| 4,221,583 | 9/1980 | Gaertner et al. | 71/86 |

FOREIGN PATENT DOCUMENTS

| 0385014 | 9/1990 | European Pat. Off. |
| 1487416 | 9/1977 | United Kingdom. |
| WO92/3448 | 3/1992 | WIPO. |
| 9203448 | 3/1992 | WIPO. |

OTHER PUBLICATIONS

Kudzin et al., Synthesis, No. 6, p. 469 (1978).
CA 109:149803r, vol. 109 (1988).
Huber, John W., III, "Synthesis of Aminoalkanephosphonic Acids from Ureidoalkanephosphates", Synthesis (Communications), 1977, pp. 883–884.
Kudzin, Z. H. et al., "Synthesis of 1-Aimoalkanephosphonates via Thioureidoalkanephosphonates", Synthesis (Communications), 1978, pp. 469–472.

*Primary Examiner*—José G. Dees
*Assistant Examiner*—Barbara S. Frazier
*Attorney, Agent, or Firm*—Joel G. Ackerman

[57] ABSTRACT

A process for the manufacture of aminomethanephosphonic acid comprises:

a) reacting a compound of formula R—CH$_2$—NH—CO—NH—CH$_2$—R' wherein R and R', which may be the same or different, represent a phosphonation leaving group with a phosphonating agent and subsequently b) hydrolysing the product of step (a) to form aminomethanephosphonic acid.

11 Claims, No Drawings

PROCESS FOR THE MANUFACTURE OF AMINOMETHANEPHOSPHONIC ACID

This invention relates to a process for the manufacture of aminomethanephosphonic acid.

Aminomethanephosphonic acid is a known compound which is useful as an intermediate in the preparation of agrochemicals. In particular a variety of processes have been described by which aminomethanephosphonic acid may be converted into the herbicide N-phosphonomethylglycine and its salts. Typical process may be found for example in U.S. Pat. No. 4,094,928 which describes the reaction of aminomethanephosphonic acid or alkyl esters thereof with glyoxal or glyoxylic esters to form a carbonylaldiminomethanephosphonate which is converted to N-phosphonomethylglycine by reduction and hydrolysis. Numerous other variants of such processes for the manufacture of N-phosphonomethylglycine from aminomethanephosphonic acid as starting material have been published.

Commercial exploitation of such processes has however been limited by the lack of an economically viable route for the manufacture of the aminomethanephosphonic acid starting material. The present invention provides a process for the manufacture of aminomethanephosphonic acid using low-cost and readily available starting materials. Furthermore the only major product of the process other than the desired aminomethanephosphonic acid is carbon dioxide and the process of the present invention is thus environmentally favoured.

According to the present invention there is provided a process for the manufacture of aminomethanephosphonic acid which comprises a) reacting a compound of formula R—CH$_2$—NH—CO—NH—CH$_2$—R' wherein R and R', which may be the same or different, represent a phosphonation leaving group with a phosphonating agent and subsequently b) hydrolysing the product of step (a) to form aminomethanephosphonic acid.

Whilst the scope of the present invention is not to be taken as being limited by any one particular theory, it is believed that reaction of the compound R—CH$_2$—NH—CO—NH—CH$_2$—R' [formula (I)[ with the phosphonating agent proceeds by reaction with the groups R and R' to produce a phosphonated or partially phosphonated urea intermediate which is then hydrolysed in stage (b) to form aminomethanephosphonic acid. A reaction scheme is illustrated in Scheme 1 for the reaction of dimethylolurea with phosphorous trichloride and in Scheme 2 for the reaction of dimethylolurea with dimethyl chlorophosphinate as described in more detail below.

Suitable groups R which are capable of acting as a phosphonation leaving group will occur to those skilled in the art. Examples include halogen, hydroxy, C$_{1-4}$ alkoxy such as methoxy, ethoxy and butoxy, aryloxy such as phenoxy and C$_{1-4}$ alkylester groups such as methoxycarbonyl and ethoxy carbonyl. Conveniently R and R' are the same. Since the function of the leaving groups R and R' is to be removed and replaced by the phosphonating agent, their exact nature is not critical, and any leaving group which is capable of being replaced by the phosphonating agent is suitable for use in the present invention. In general however, a simple leaving group is commercially preferred and dimethylolurea, in which R and R' are both hydroxy is an especially preferred starting material.

Suitable phosphonating agents include (i) phosphorous trichloride, (ii) phosphorous acid, (iii) a dialkyl phosphite, for example a di-C$_{1-7}$ alkyl phosphite such as dimethylphosphite or diethylphosphite, (iv) a compound of formula (VI)

$$(Cl)_nP(OR^1)_{3-n} \quad (VI)$$

or a mixture of such compounds, wherein n is 1 or 2 and R$^1$ is optionally substituted alkyl, for example optionally substituted C$_{1-7}$ alkyl or optionally substituted aryl, for example optionally substituted phenyl or (v) phosphorous trichloride in admixture with an alcohol of formula R$^1$OH wherein R$^1$ is as herein defined.

A mixture of phosphonating agents may be used if desired.

In the compound of formula (VI) n is preferably 1. Compounds of formula (VI) wherein n is 1 are known compounds which may be described by a variety of trivial names including dialkyl phosphochloridite, dialkyl chlorophosphite and dialkyl chlorophosphinate. Such compounds are referred to herein as dialkyl chlorophosphinates, for example diethyl chlorophosphinate. When n is 1, the two groups R$^1$ may be the same or different. The two groups R$^1$ may if desired be linked to form a bridging alkyl group. The two groups R$^1$ are conveniently the same.

Whilst optional substituents such as halogen and nitro may be present in the alkyl group(s) R$^1$, there is no particular benefit in the presence of such substituents and the group(s) R$^1$ are preferably unsubstituted C$_{1-7}$ such as methyl, ethyl, propyl, butyl and pentyl.

The compound of formula (VI) is conveniently prepared by the reaction of phosphorous trichloride with an alcohol R$^1$OH. The compound of formula (VI) wherein n is 1 is for example prepared by reacting two molar proportions of the alcohol with 1 molar proportion of phosphorous trichloride. It will be appreciated that use of less than two molar proportions of alcohol may be expected to produce a proportion of the compound of formula (VI) wherein n is 2. Use of more than two molar proportions of alcohol will tend to form a proportion of trialkyphosphite.

Whilst the compound of formula (VI) may be isolated from the mixture of the alcohol R$^1$OH and phosphorous trichloride and thereafter used as the phosphonating agent, the phosphorous trichloride in admixture with an alcohol of formula R$^1$OH may itself be used as a phosphonating agent the preferred proportions being as indicated above. The nature of the species present in such a mixture during the course of the phosphonation reaction may be complex and the scope of the present invention is not to be taken as being limited by the presence of any particular species, whether a compound of formula (VI) or otherwise, in the mixture of phosphorous trichloride and the alcohol of formula R$^1$OH when the said mixture is used as phosphonating agent.

Whether the phosphonating agent is a compound of formula (VI) formed by the reaction of phosphorous trichloride and the alcohol or whether the phosphonating agent is an admixture of phosphorous trichloride and the alcohol R$^1$OH, it is preferred to use from 1 to 2.2 moles of alcohol R$^1$OH per mole of phosphorous trichloride, for example from 1.8 to 2.2 moles of alcohol R$^1$OH per mole of phosphorous trichloride and in particular about 2 moles of alcohol R$^1$OH per mole of phosphorous trichloride.

If desired the hydrochloric acid which is a product of the reaction may first be removed, for example by sparging with a dry non-oxidising gas such as nitrogen.

Phosphorous acid is suitably used as a phosphonating agent in combination with acetic acid and acetic anhydride. Dialkyl phosphites may be used as phosphonating agents, but we have found that reaction temperatures of the order of 100° C. are required to obtain reasonable yields of product whereas preferred phosphonating agents give excellent yields under milder conditions.

Phosphorous trichloride or a dialkyl chlorophosphinate, such as diethyl chlorophosphinate or dibutylchlorophosphinate, or a mixture of phosphorous trichloride and an alchohol such as ethanol or butanol, are especially preferred phosphonating agents.

Reaction stage (a) suitably takes place under substantially anhydrous and non-oxidising conditions.

Reaction stage (a) may take place in the absence of a solvent if desired, provided the phosphonating agent itself is capable of dissolving or suspending the compound of formula (I) and forming an effective reaction medium. If desired excess phosphonating agent may be used to provide an effective reaction medium, for example to reduce the viscosity of the medium and permit effective stirring or agitation. Alternatively an anhydrous solvent may be used with the phosphonating agent. Suitable solvents are inert under the reaction conditions, and in particular are inert to attack by the phosphonating agent. Examples of suitable solvents include ketones, chlorinated hydrocarbons, aromatic solvents, nitriles and anhydrous carboxylic acids and esters. Especially preferred solvents are nitriles such as acetonitrile, benzonitrile, propionitrile, and butyronitrile and carboxylic acids such as acetic acid and ethyl formate. Combinations of solvents such as a mixture of ethyl formate and acetic acid may also be used. Subsequent isolation of the aminomethanephosphonic acid product may be facilitated by the use of a water-immiscible solvent as described in greater detail below.

To provide a mobile reaction medium and facilitate stirring, it is preferred to use at least 1 part by weight of solvent per 1 part by weight of the compound of formula (I). Thus the proportion of reaction solvent is preferably from 1 part by weight of solvent per 1 part by weight of the compound of formula (I) to 20 parts by weight of solvent per 1 part by weight of the compound of formula (I). It is commercially undesirable to use excess solvent and it is preferred to use from 1 part by weight of solvent per 1 part by weight of the compound of formula (I) to 5 parts by weight of solvent per 1 part by weight of the compound of formula (I)

The reaction stage (a) preferably takes place at a temperature within the range from 0° C. to 50° C., although we have found that the reaction proceeds slowly at temperatures as low as −30° C. in a suitable solvent such as acetonitrile. There is in general no particular advantage in undertaking reaction stage (a) at temperatures above 50° C. as by-product formation may tend to reduce the yield. The reaction of stage (a) is exothermic and cooling may be necessary to maintain the desired temperature.

A stoichiometric proportion of reactants is conveniently used in stage (a), although a slight excess of either the phosphonating agent or the compound of formula (I) may be used if desired. As indicated above, a larger excess of phosphonating agent may be used if it is desired to use the phosphonating agent as the reaction solvent.

The hydrolysis stage (b) may take place by the addition of water to the reaction medium resulting from stage (a), optionally after the removal of any water-miscible solvent which is used. If desired acid or base may be added to facilitate the hydrolysis stage. Acidic hydrolysis is preferred, for example using dilute mineral acid such as hydrochloric acid. Conveniently the acid hydrolysis takes place in the presence of a mineral acid of strength from 0% to 36% by weight, for example from 0.3% to 4.0% by weight. When phosphorous trichloride is used as the phosphonating agent, addition of acid to the hydrolysis stage may be unnecessary since acid is produced in stage (a), it is believed as a result of the phosphonation or partial phosphonation to produce the urea intermediate (Scheme 1).

When a water-immiscible solvent is used in reaction stage (a), the addition of water or acid will cause the intermediate phosphonated product (II) in Scheme 1 and (II') in Scheme 2) to transfer into the aqueous phase. The aqueous and organic phases may then be separated so that the hydrolysis step (b) takes place in the aqueous phase whilst the organic phase is optionally re-cycled.

When the reaction (a) takes place in the presence of a water-miscible solvent it may be desirable to separate the solvent prior to the completion of the hydrolysis step (b) and replace it with a water-immiscible solvent to facilitate solvent recovery and re-cycle. Thus for example the water-miscible solvent may be removed by distillation and replaced by a water-immiscible solvent. If the water-immiscible solvent is higher boiling than the water-miscible solvent and does not form an azeotrope with it, the water-immiscible solvent may be added prior to or during the distillation to maintain an effective working volume and assist in the removal of substantially all the water-miscible solvent. Thus for example if acetonitrile is the water-immiscible solvent, xylene or benzonitrile may be added and the mixture heated to the boiling point of the acetonitrile which is removed and re-cycled. Addition of water or acid then causes the extraction of the phosphonated intermediate into the aqueous phase for subsequent hydrolysis or completion of the hydrolysis. The water-immiscible solvent phase may subsequently also be re-cycled.

The hydrolysis stage (b) is shown in Schemes I and 2 as a single step. In practice, it is believed that the hydrolysis takes place in two steps as in Scheme 3. Step (i) is believed to take place very readily under mild conditions, for example simply on contact with water under ambient conditions or at reflux under ambient pressure. Step (ii) requires rather more stringent conditions as discussed below. We have found that in some circumstances, and when a water-miscible solvent is to be removed, there may be advantages in adding sufficient water (i.e. up to 4 moles of water per mole of phosphonated intermediate (II) or (II') to effect step (i) hydrolysis prior to removal of the water-miscible solvent and its replacement by the water-immiscible solvent, so that species (IV) (rather than species (II) or (II')) is present during the distillation to remove water-miscible solvent and is subsequently extracted into the aqueous phase for complete hydrolysis.

Thus according to a further aspect of the present invention there is provided a process for the manufacture of aminomethanephosphonic acid which comprises reacting a compound of formula R—CH$_2$—NH—CO—NH—CH$_2$—R' wherein R and R', which may be the same or different, represent a phosphonation leaving group with a phosphonating agent which is phosphorous trichloride or a dialkyl chlorophosphinate of formula ClP(OR$^1$)$_2$ wherein R$^1$ is C$_{1-7}$ alkyl or a with a phosphonating agent which is mixture of phosphorous trichloride and an alcohol of formula R$^1$OH in the presence of a water-miscible solvent to form a compound of formula (II) when the phosphonating agent is phosphorous trichloride and a compound of formula (II') when the phosphonating agent is a dialkyl chlorophosphinate or is a mixture of phosphorous trichloride and the alcohol R$^1$OH;

2) hydrolysing the compound of formula (II) or (II') with water under mild conditions to form a compound of formula (IV)

3) separating the water-miscible solvent by distillation and replacing it by a water-immiscible solvent 4) adding water and extracting the compound of formula (IV) into the aqueous phase thus formed and 5) hydrolysing the aqueous phase from stage (4) at a temperature of from 100° C. to 200° C., the pressure being adjusted accordingly, thereby forming aminomethane-phosphonic acid.

In a further variant, an alcohol, for example a $C_{1-7}$ alkyl alcohol such as $R^1OH$ or a higher alcohol such as a $C_5$ to $C_{15}$ alcohol, for example 2-ethylhexanol, may be used in place of water (Scheme 4) so that species (V) (rather than species (II)) is present during the distillation to remove water-miscible solvent and is subsequently extracted into the aqueous phase for complete hydrolysis.

The choice of the species present during the distillation to remove water-miscible solvent (according to Scheme 1, 2, 3 or 4) provides flexibility in the process and may be governed for example by the relative thermal stabilities of the species at the boiling point of the water-immiscible solvent.

The hydrolysis step (b), either as a combination of steps (i) and (ii) as illustrated in Schemes 1 and 2 or as the second step (ii) in a split process such as illustrated in Schemes 3 and 4, preferably takes place at a temperature in the range from ambient to reflux, optionally with the application of external pressure. Thus the hydrolysis preferably takes place at a temperature of from 100° C. to 200° C., for example about 150° C., the pressure being adjusted accordingly. Carbon dioxide is produced during the hydrolysis (Scheme 1) and is preferably vented during the hydrolysis.

It is preferred to add from 5 to 50 moles of water per mole of the starting material of formula (I) during the overall course of the hydrolysis. Additional water may be added if desired but the presence of excess water may add to the difficulty of subsequent isolation stages. It is generally preferred to add the minimum quantity of water which is necessary to effect the hydrolysis and to dissolve the product of the reaction.

Compounds of formula (I) are either known compounds or may be prepared using analogous methods to those used for the preparation of known compounds. Thus for example dimethylolurea is conveniently prepared by the reaction of urea and formaldehyde. The compound of formula (I) may be supplied to the reaction either as a dry solid or as a solution or slurry in an anhydrous solvent, for example as a solution or slurry in the solvent which is to be used for the reaction stage (a).

The product of the hydrolysis stage (b) will usually be an aqueous solution containing the desired aminomethanephosphonic acid product. The aminomethanephosphonic acid may be recovered from the aqueous solution by methods known to those skilled in the art, for example by crystallisation. In general however the aminomethanephosphonic acid prepared by the process of this invention will be used as the starting material in a further reaction, for example as a starting material for the preparation of N-phosphonomethylglycine. It will often be the case that an aqueous solution of aminomethanephosphonic acid is a suitable feedstock for the further reaction, optionally with the provision of an intermediate purification stage. In this instance it may be unnecessary to isolate the aminomethanephosphonic acid product from the aqueous solution.

Thus according to a further aspect of the present invention there is provided a process wherein the aminomethanephosphonic acid product is further reacted without being isolated from aqueous solution to yield N-phosphonomethylglycine.

As noted above, when a water-immiscible solvent is used for the reaction stage (a) or when a water-miscible solvent used in stage (a) is subsequently replaced by a water-immiscible solvent, the water-immiscible solvent phase may then conveniently be re-cycled to a further reaction stage (a) on a continuous or semi-continuous basis.

When a compound of formula (VI) or a mixture of phosphorous trichloride and the alcohol is used as the phosphonating agent, one product of hydrolysis is the alcohol $R^1OH$ (Scheme 2). If $R^1OH$ is a water-immiscible alcohol such as that derived from a $C_4$ or $C_5$ alkyl group $R_1$. (butanol or pentanol respectively), this opens the possibility of separating and re-cycling the alcohol. Lower alcohols may if desired be recovered and re-cycled by alternative means, for example by distillation during the hydrolysis stage.

The order of addition of the reactants in stage (a) may be varied as desired. Thus for example it is convenient to add the compound of formula (I) and the phosphonating agent to the solvent. It is equally possible however to add the phosphonating agent to a solution or slurry of the compound of formula (I) in the reaction solvent or to add a solution or slurry of the compound of formula (I) to a solution of the phosphonating agent in the reaction solvent. When a compound of formula (VI) is used as phosphonating agent and is generated in situ by the reaction of phosphorous trichloride and the alcohol $R^1OH$, it is not essential to pre-form the compound of formula (VI) prior to addition to the reaction medium. Thus for example the phosphorous trichloride may be added to the reaction solvent followed by the alcohol.

The invention is illustrated by the following Example in which all parts and percentages are by weight unless otherwise stated.

EXAMPLE 1

Phosphorus trichloride 25.7 g (0.183 g mol) was charged to a 250 ml round bottom flask and agitation was started. Dimethylol urea log (0.083 g mol) was added over 30 minutes with stirring. A further log (0.073 g mol) of phosphorous trichloride was added to facilitate the stirring of the reaction mass and the reaction was held at ambient temperature for 3 hours. Dry acetic acid 20 g (0.333 g mol) was added and the reaction mass was heated to 50° C. and held at this temperature for 3 hours. The temperature was raised to 100° C. and held for 4 hours. The reaction was then cooled to 60° C. and water (50 g) was added over 15 minutes. The reaction was heated to reflux (104° C.) and held for 20 hours.

Analysis of the resultant aqueous solution indicated the presence of aminomethanephosphonic acid in excess of 504 yield.

EXAMPLE 2

Acetonitrile (100g, 2.44 g mol) was charged to a 500 ml round bottom flask fitted with an agitator, thermometer and condenser. The apparatus was flushed with argon and the solvent cooled to 10° C. Dimethylol urea (51.6 g, 0.409 g mol) and phosphorous trichloride (105.9 g, 0.766 g mol) were each added in ten equal portions over a period of 3 hours with stirring. The reaction was stirred at ambient temperature for 16 hours after which time the dimethylol urea starting material which had been present as a slurry had all dissolved. Water (27 g) was added slowly whilst maintaining the temperature below 30° C. The reaction mass was heated at atmospheric pressure to a temperature sufficient to distill the acetonitrile and xylene (100 g) was added slowly during the distillation. Water (100 g) was added and the lower, aqueous phase containing bisphonomethylurea (compound (IV) in Scheme 3) was separated.

Dilute hydrochloric acid (200 ml of 3.654 w/w strength) was added to the aqueous layer which was heated for 10 hours under sufficient pressure to maintain the temperature at 150° C., whilst the pressure vessel was periodically vented to remove carbon dioxide formed.

The yield of aminomethanephosphonic acid was determined as 85% by nmr analysis and 83.2% by HPLC analysis.

EXAMPLE 3

Butyronitrile (20 g) was charged to a 100 ml round bottom flask fitted with an agitator, thermometer and condenser. The apparatus was flushed with argon and the solvent cooled to 10° C. Dimethylol urea (10.3 g at 95% strength) and phosphorous trichloride (21.3 g) were each added in five equal portions over a period of about one hour with a ten minute delay between one phosphorous trichloride addition and the subsequent dimethylolurea addition. The reaction was stirred at room temperature overnight and then heated to 55° C. and held at that temperature for 1 hour. Water (20 g) was added and the solid precipitate which formed rapidly dissolved in the excess water. The two layers were separated to give a clear colourless butyronitrile layer and a clear aqueous solution of bis(phosphonomethyl)urea. The yield of bis(phosphonomethyl)urea was 80% as determined by nmr. Hydrolysis of the aqueous layer took place as in Example 1 with quantitative conversion to aminomethanephosphonic acid.

EXAMPLE 4

The procedure of Example 2 was repeated using acetic acid and ethyl formate respectively as water-miscible solvents.

EXAMPLE 5

The procedure of Example 3 was repeated using toluene, benzonitrile, propionitrile, and 2-methyl-glutaronitrile as water-immiscible solvents.

EXAMPLE 7

Phosphorous trichloride (23.4 g) and acetonitrile (100 g) were charged into a 250 ml flask. The dimethyl ether of dimethylolurea (the compound of formula (I) wherein R and R' are both —$CH_2$—$OCH_3$) (12.3 g) was added portionwise. The mixture was stirred for 18 hours at ambient temperature and was then heated to 50° C. and held at that temperature for 2 hours. A white precipitate was formed and hydrogen gas was evolved. The reaction mixture was heated to reflux and held at that temperature for 2 hours. The acetonitrile solvent was removed from the reaction mixture by distillation, adding 30 ml of xylene near the end of the distillation. The reaction mixture was drowned out with 60 g of water and then separated into two layers. Water (40 g) was removed from the aqueous layer by vacuum distillation to give a solid product.

The product thus obtained was dissolved in 40 g water and 11.9 g of 36% hydrochloric acid and was heated to reflux at atmospheric pressure. (In commercial practice it would not be necessary to remove water from the aqueous layer to give a solid product and then add further water. It was done in this instance so that HCl was removed during the distillation and hydrolysis then took place using acid of an exactly known concentration). Hydrolysis was completed over a period of 8 days to yield 48.3% aminomethanephosphonic acid as determined by HPLC analysis.

EXAMPLE 8

The procedure of Example 7 was repeated using as starting material a compound of formula (I) wherein R and R' are the same and are —$CH_2$—O—$C_4H_9$. The yield was 35.5% of aminomethane-phosphonic acid as determined by HPLC.

EXAMPLE 9

A solution of 32.8 g of phosphorous acid in 60 ml acetic acid was added dropwise to 112.2 g of acetic anhydride with cooling over a period of 1 hour. Dimethylolurea (24 g) was added portionwise over 50 minutes whilst the temperature was maintained between 10° to 15° C. The solution was stirred for a further 20 minutes at 10° C. The reaction mixture was then heated to reflux and held at that temperature for two and a half hours. After cooling to ambient temperature 12.2 g of water was added dropwise with cooling and the temperature was maintained in the range 25°–30° C. The solution was then heated to reflux and held at that temperature for 2 hours. After cooling, the acetic acid was removed by vacuum distillation to yield an off-white solid.

The solid was dissolved in water (40 g) and hydrochloric acid (11.9 g of a 36% solution) and heated to reflux at atmospheric pressure. Hydrolysis was complete after 7 days and the yield of aminomethanephosphonic acid was 17.8% as determined by HPLC.

EXAMPLE 10

The procedure of Example 9 was repeated except that the hydrolysis took place under alkaline conditions. An aqueous solution of bis(phosphonomethyl)urea (82.7 g at 30% strength; 0.1 g mole) and sodium hydroxide solution (51.1 g at 47% strength 0.6 g mole) was heated at 100° C. for 120 hours. The yield of aminomethanephosphonic acid disodium salt was 10.55 g (95% based on the bis(phosphonomethyl)urea charged)

EXAMPLE 11

Dimethylolurea (6 g) was added to acetonitrile (100 ml) and diethyl chlorophosphinate (15.65 g) was added dropwise with cooling and stirring over a period of a half hour. The reaction mixture became clear with essentially all the dimethylolurea having passed into solution. Water (50 ml) and hydrochloric acid (10 ml of 0.1M) were added and the reaction flask was heated to distill the acetonitrile. Two portions (30 ml each) of ethanol were added to azeotrope with the water and effect further distillation and the mixture was then heated to reflux under atmospheric pressure. After 7 days at reflux the hydrolysis was complete and the yield of aminomethanephosphonic acid was 88% as determined by phosphorous nmr.

EXAMPLE 12

Acetonitrile (25 ml) was charged to a flask fitted with condenser, thermometer, agitator and dropping funnel and the whole was cooled to 0°– 10° C. Phosphorous trichloride (7 g) was added followed by ethanol (4.6 g) added slowly over half an hour whilst the temperature was maintained at 0°– 10° C. The mixture was stirred for one hour and solid dimethylolurea (3.3 g) was added over half an hour whilst maintaining the temperature at 0°–10° C. The reaction mixture was allowed to warm to ambient temperature and was stirred for 3 hours. The acetonitrile was then removed by vacuum distillation. Water (50 ml) was added and the aqueous mixture was heated at reflux under atmospheric pressure of 1 hour. Bisphosphonomethylurea was obtained in 80% yield and is converted to aminomethanephosphonic acid in essentially quantitative yield.

EXAMPLE 13

The procedure of Example 12 was repeated using toluene in place of acetonitrile. After the phosphonation reaction was complete, water (50 ml) was added and the phases were separated. The aqueous phase was heated at reflux under atmospheric pressure for 1 hour. Bisphosphonomethylurea was obtained in 69% yield and is converted to aminomethane-phosphonic acid in essentially quantitative yield.

EXAMPLE 14

The procedure of Example 2 was repeated up to the stage at which the dimethylol urea starting material which had been present as a slurry had all dissolved.

2-Ethylhexanol (200.7 g) was then added slowly whilst maintaining the temperature below 30° C. The reaction mass was heated at atmospheric pressure to a temperature sufficient to distill acetonitrile. Water (100 g) was added and the reaction mass was heated to reflux for 2 hours. The reaction mass was cooled and the layers separated to give an aqueous solution of bis(phosphonomethyl)urea which was hydrolysed as in Example 2.

EXAMPLE15

Diethylphosphite (41.4 g) and dimethylolurea (10 g) were charged to a 100 ml round bottom flask and heated to 120° C. Heating was continued for 20 hours during which time a small amount of distillate (7.2 g) was collected. The excess diethylphosphite was distilled under reduced pressure and water (40 ml) was charged. The mass was refluxed for 2 hours in the presence of 0.8 g 36% HCl. The yield of bis(phosphonomethyl)urea was 66% as determined by nmr, which on hydrolysis is converted in esstentially quantitative yield to aminomethanephosphonic acid.

EXAMPLE 15

Phosphorus trichloride (7.0 g) was charged to a 100 ml round bottom flask and methanol (3.2 g) was added slowly whilst keeping the temperature of the reaction below 20° C. Benzonitrile (25 ml) was charged and dimethylolurea (3.3 g) was added in portions over 30 minutes. The mixture was stirred at room temperature overnight, water (50 ml) was added and the two phases were separated. The aqueous phase was refluxed for 2 hours to give an aqueous solution of bis(phosphonomethyl)urea in 82% yield, which on hydrolysis is converted in esstentially quantitative yield to aminomethanephosphonic acid.

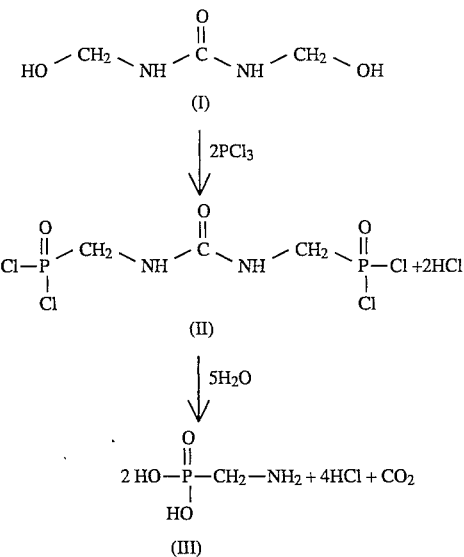

CHEMICAL FORMULAE
(IN DESCRIPTION)
Scheme 1

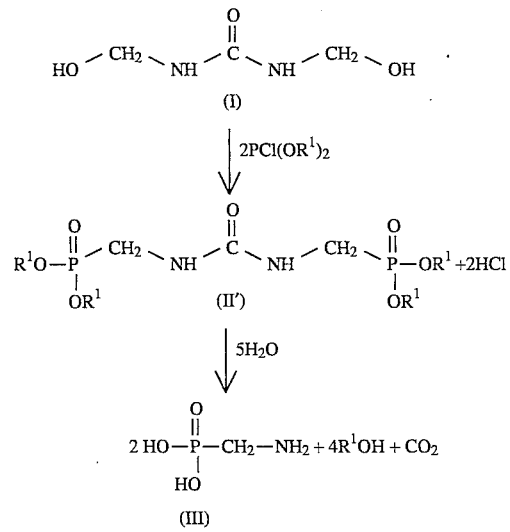

CHEMICAL FORMULAE
(IN DESCRIPTION)
Scheme 2

CHEMICAL FORMULAE
(IN DESCRIPTION)
Scheme 3

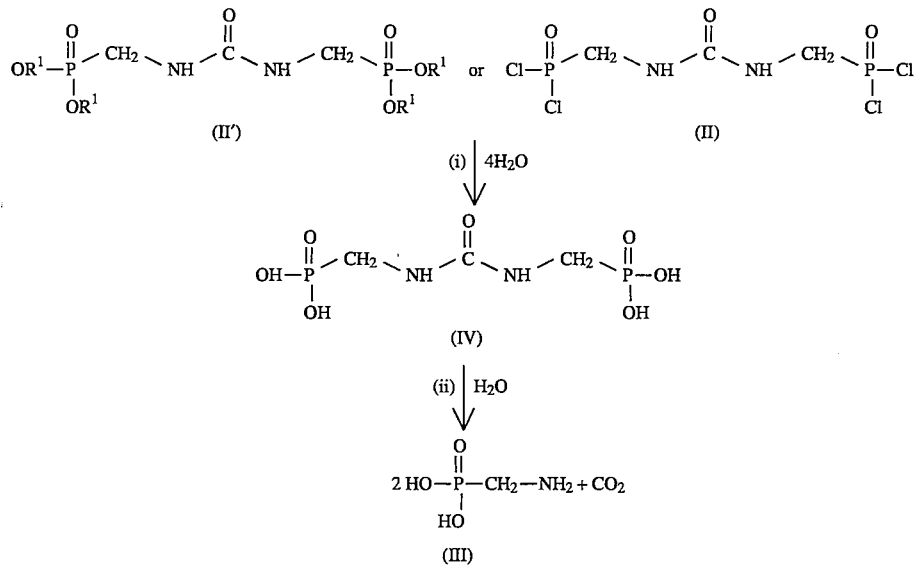

CHEMICAL FORMULAE
(IN DESCRIPTION)
Scheme 4

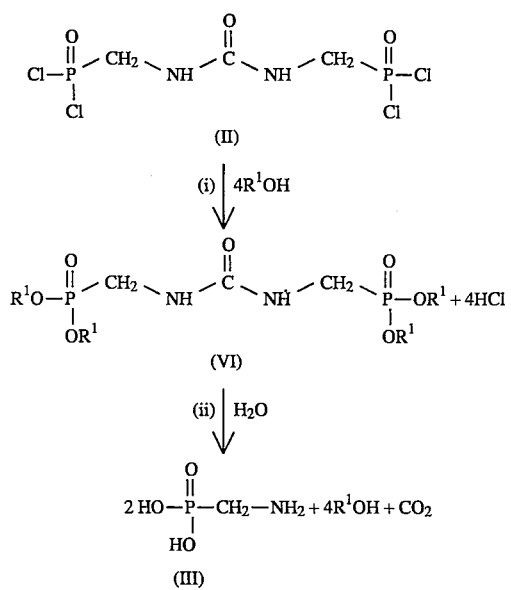

We claim:

1. A process for the manufacture of aminomethanephosphonic acid which comprises a) reacting a compound of formula R—CH$_2$—NH—CO—NH—CH$_2$—R' wherein R and R', which may be the same or different, represent a phosphonation leaving group with a phosphonating agent and subsequently b) hydrolysing the product of step (a) to form aminomethanephosphonic acid.

2. A process according to claim 1 wherein R and R' are the same and represent hydroxy or C$_{1-4}$ alkoxy.

3. A process according to claim 1 wherein the phosphonating agent is selected from the group consisting of (i) phosphorous trichloride, (ii) phosphorous acid, (iii) a dialkyl phosphite, (iv) a compound of formula (VI)

$$(Cl)_nP(OR^1)_{3-n} \qquad (VI)$$

or a mixture of such compounds, wherein n is 1 or 2 and R$^1$ is optionally substituted alkyl or optionally substituted phenyl and (v) phosphorous trichloride in admixture with an alcohol of formula R$^1$OH wherein R$^1$ is as herein defined.

4. A process according to claim 3 wherein the phosphonating agent is a compound of formula (VI) wherein n is 1 and R$^1$ is C$_{1-7}$ alkyl.

5. A process according to claim 3 wherein the phosphonating agent is a mixture of phosphorous trichloride and an alohol of formula R$^1$OH wherein R$^1$ is C$_{1-7}$ alkyl and there is used from 1.8 to 2.2 moles of alcohol R$^1$OH per mole of phosphorous trichloride.

6. A process according to claim 1 wherein the reaction (a) takes place at a temperature of from 0° C. to 50° C.

7. A process according to claim I wherein the hydrolysis reaction (b) takes place at a temperature of from 100° C. to 200° C., the pressure being adjusted accordingly.

8. A process according to claim 1 wherein the reaction (a) takes place in the presence of a solvent which is a ketone, a chlorinated hydrocarbon, an aromatic solvent, a nitrile or an anhydrous carboxylic acid or ester.

9. A process according to claim i wherein the reaction (a) takes place in the presence of a water-miscible solvent which is separated prior to the completion of the hydrolysis stage (b) and is replaced by a water-immiscible solvent.

10. A process for the manufacture of aminomethanephosphonic acid which comprises 1) reacting a compound of formula R—CH$_2$—NH—CO—NH—CH$_2$—R' wherein R and R', which may be the same or different, represent a phosphonation leaving group with a phosphonating agent which is selected from the group consisting of phosphorous trichloride, a dialkyl chlorophosphinate of formula ClP(OR$^1$)$_2$ wherein $R^1$ is $C_{1-7}$ alkyl, and a mixture of phosphorous trichloride and an alcohol of formula $R^1OH$ in the presence of a water-miscible solvent to form a compound of formula (II) when the phosphonating agent is phosphorous trichloride and a compound of formula (II') when the phosphonating agent is a dialkyl chlorophosphinate or a mixture of phosphorous trichloride and the alcohol $R^1OH$;

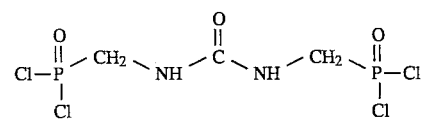
(II)

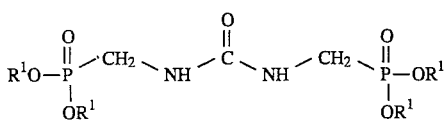
(II')

2) hydrolysing the compound of formula (II) or (II') with water under mild conditions to form a compound of formula (IV):

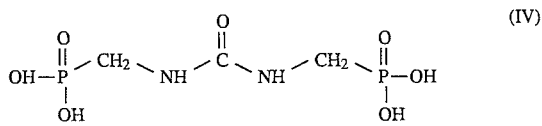
(IV)

3) separating the water-miscible solvent by distillation and replacing it by a water-immiscible solvent.

4) adding water and extracting the compound of formula (IV) into the aqueous phase thus formed and 5) hydrolysing the aqueous phase from stage (4) at a temperature of from 100° C. to 200° C., the pressure being adjusted accordingly thereby forming aminomethanephosphonic acid.

11. A process according to claim i wherein the aminomethanephosphonic acid product is further reacted without being isolated to form N-phosphonomethyglycine.

* * * * *